(12) United States Patent
You et al.

(10) Patent No.: US 8,518,700 B2
(45) Date of Patent: Aug. 27, 2013

(54) COMPOSITION FOR REPROGRAMMING SOMATIC CELLS TO GENERATE INDUCED PLURIPOTENT STEM CELLS, COMPRISING BMI1 AND LOW MOLECULAR WEIGHT SUBSTANCE, AND METHOD FOR GENERATING INDUCED PLURIPOTENT STEM CELLS USING THE SAME

(75) Inventors: Seungkwon You, Yongin-si (KR); Jai-Hee Moon, Seoul (KR); Jun Sung Kim, Guri-si (KR); Byung Sun Yoon, Seoul (KR); Jung Han Lee, Seoul (KR); Eun Kyoung Jun, Seongnam-si (KR); June Seok Heo, Seoul (KR); Ji Hyun Kim, Seoul (KR); Ji Hye Hwang, Bucheon-si (KR); Su Hyun Gwon, Bucheon-si (KR)

(73) Assignee: Korea University Research and Business Foundation, Seoul (KR)

( * ) Notice: Subject to any disclaimer, the term of this patent is extended or adjusted under 35 U.S.C. 154(b) by 11 days.

(21) Appl. No.: 13/103,611

(22) Filed: May 9, 2011

(65) Prior Publication Data

US 2011/0275157 A1    Nov. 10, 2011

(30) Foreign Application Priority Data

May 10, 2010   (KR) .................. 10-2010-0043695
May 10, 2010   (KR) .................. 10-2010-0043697
May 10, 2010   (KR) .................. 10-2010-0043698

(51) Int. Cl.
*C12N 15/85* (2006.01)
*C12N 5/0735* (2010.01)

(52) U.S. Cl.
USPC .................. 435/455; 435/377; 435/325

(58) Field of Classification Search
USPC .................. 435/455, 325, 377
See application file for complete search history.

(56) References Cited

U.S. PATENT DOCUMENTS 5,824,837 A * 10/1998 Chen et al. .................. 800/3
5,843,780 A * 12/1998 Thomson .................. 435/363
2009/0047263 A1   2/2009 Yamanaka et al.

FOREIGN PATENT DOCUMENTS

WO   WO/2011/082038   * 7/2011

OTHER PUBLICATIONS

Suh et al. J Cell Physiol 226(12):3422-3432, 2011.*
Silva, et al., "Promotion of Reprogramming to Ground State Pluripotency by Signal Inhibition," PLOS Biology, (2008), vol. 6, Iss. 10, pp. 2237-2247.
Shi, et al., "Induction of Pluripotent Stem Cells from Mouse Embryonic Fibroblasts by Oct4 and Klf4 with Small-Molecule Compounds," Cell Stem Cell, (2008), vol. 3, pp. 568-574.
Feng, et al., "Molecules that Promote or Enhance Reprogramming of Somatic Cells to Induced Pluripotent Stem Cells," Cell Stem Cell, (2009), vol. 4, pp. 301-312.

* cited by examiner

*Primary Examiner* — Marcia S Noble
(74) *Attorney, Agent, or Firm* — Edwards Wildman Palmer LLP

(57) ABSTRACT

Provided is a composition for reprogramming somatic cells to generate embryonic stem cell-like cells, comprising: a) a Bmi1 (B cell-specific Moloney murine leukemia virus integration site 1) protein or a nucleic acid molecule encoding the Bmi1 protein; and b) at least one low molecular weight substance selected from the group consisting of a set of a MEK/ERK (mitogen-activated protein kinase/extracellular regulated kinase) inhibitor and a GSK (glycogen synthase kinase) inhibitor, a set of a G9a HMTase (G9a histone methyltransferase) inhibitor and a DMNT (DNA methyltransferase) inhibitor, and a histone deacetylase inhibitor. Also, a method is provided for reprogramming somatic cells to generate embryonic stem cell-like cells using the composition. In addition to reducing the number of the reprogramming factors conventionally needed, the composition and method allow the generation of pluripotent embryonic stem cell-like cells which have high potential in the cell therapy of various diseases.

7 Claims, 10 Drawing Sheets

COMPOSITION FOR REPROGRAMMING SOMATIC CELLS TO GENERATE INDUCED PLURIPOTENT STEM CELLS, COMPRISING BMI1 AND LOW MOLECULAR WEIGHT SUBSTANCE, AND METHOD FOR GENERATING INDUCED PLURIPOTENT STEM CELLS USING THE SAME

CROSS-REFERENCE TO RELATED PATENT APPLICATIONS

This application claims the benefit to Korean Patent Application Nos. 10-2010-0043695, 10-2010-0043697, and 10-2010-0043698, each filed on May 10, 2010 in the Korean Intellectual Property Office. The entire contents of the aforementioned patent applications are incorporated herein by reference.

BACKGROUND OF THE INVENTION

1. Field of the Invention

The present subject matter relates to a composition for reprogramming somatic cells to generate embryonic stem cell-like cells, comprising Bmi1 and a low molecular weight substance, and a method for generating embryonic stem cell-like cells using the same. In particular, the present subject matter relates to a composition for reprogramming somatic cells to generate embryonic stem cell-like cells by introducing Bmi1 into the somatic cells and treating the cells with low molecular weight substances including a MEK inhibitor and a GSK inhibitor, and a method for generating embryonic stem cell-like cells using the same.

2. Description of the Related Art

Unlike normal somatic cells, stem cells have self-renewal, that is, the ability to go through numerous cycles of cell division while maintaining a state of undifferentiation, and potency, that is, the capacity to differentiate into specialized cell types under suitable conditions. Potency specifies the differentiation potential of the stem cells, and is typically divided into pluripotency, multipotency and unipotency. Therefore, the technique of allowing the stem cells to undergo self-renewal in cell cultures and transforming them into specialized cells has high potential in the cell therapy of various diseases.

Various stem cells including hematopoietic stem cells, bone marrow stem cells and neural stem cells are present in adults and can be isolated from the patients themselves and thus can be used in medical therapies without inducing immune rejection response. Cell therapy with adult stem cells solves the difficulty of securing donors for organ implantation.

However, adult stem cells have been so far known to remain multipotent. That is, tissue-specific stem cells are able to differentiate into a number of cells, but only those of a closely related family of cells. Disclosed in many reports are the effects that stem cells isolated from the central nervous system (Science 255, 1707-1710 1992; Science 287, 1433-1438 2000), the bone marrow (Science 276, 71-74, 1997; Science 287, 1442-1446, 2000; Science 284, 143-147, 1999), the retina (Science 287, 2032-2036, 2000) and the skeletal muscle (Proc. Natl. Acad. Sci. USA 96, 14482-14486, 1999; Nature 401, 390-394, 1999) undergo differentiation into the cells of closely related tissue. For example, hematopoietic stem cells can be differentiated into blood-related cells, neural stem cells into neurons or glial cells, and bone marrow stem cells into mesodermal cells. Moreover, adult stem cells, although able to theoretically undergo infinite self-renewal, have been reported with regard to difficulty in proliferating them in vitro. It is practically difficult to isolate a number of cells from patients.

Pluripotent stem cells are a wonderful resource overcoming the drawbacks of adult stem cells. Pluripotent stem cells can differentiate into nearly any cell and are allowed to replicate infinitely in vitro. Among the pluripotent stem cells known thus far are embryonic stem cells, embryonic germ cells and embryonic carcinoma cells, with most studies focusing on using embryonic stem cells for the purposes of differentiation into specific cells, functionality in animal models of diseases, and therapeutic potency for various diseases.

Nonetheless, the clinical use of embryonic stem cells, like adult stem cells, encounters barriers that must be overcome. Above all, because isolating embryonic stem cells results in the death of the fertilized human embryo, this raises ethical issues. Also, there is the problem of immunological rejection when differentiated cells derived from embryonic stem cells are implanted into patients.

A variety of approaches have been suggested to the above-mentioned problems, of which reprogramming differentiated cells into pre-differentiated cells has attracted the most attention. Reprogramming is a generic term expressing the induction of differentiated cells to dedifferentiate into pluripotent stem cells such as embryonic stem cells, generally achieved by 1) nuclear transfer, 2) cell fusion, 3) cell extract treatment, and 4) dedifferentiation technology for induced pluripotent stem cell (iPS cell) (Cell 132, 567-582, 2008).

iPS cell technology has succeeded in generating cells closer to embryonic stem cells than has any other technology. Since 2006 when iPS cells were first produced, a significant number of research articles have been issued. In principle, stem cells similar to embryonic stem cells, e.g., iPS cells, are established by transfection of four genes (reprogramming inducing genes; Oct4, Sox2, Klf4, and C-Myc/Oct4, Sox2, Nanog, Lin28) into mouse or human somatic cells, followed by culturing for a long period of time under conditions specialized for embryonic stem cells. These iPS cells have been demonstrated to resemble embryonic stem cells in their gene expression profile, epigenetics, in vitro/in vivo differentiation into all three germ layers, teratoma formation, chimeric mouse generation and the chimeric mouse's competency for germline transmission (Cell 126, 663-676, 2006; Science 318, 1917-1920, 2007).

However, too many gene factors used in reprogramming have made it difficult to understand the molecular mechanisms underlying reprogramming. To realize the full potential of iPS cells in practical clinical use, it will be essential to improve the reprogramming technology, although established, and to evaluate each generated iPS cell line for safety and efficacy.

Recent research reports have it that the inactivation of the tumor suppressor gene p53 markedly increases the efficiency of iPS (Nature 460, 1132-1135, 2009). $p19^{Arf}$ and $p16^{Ink4a}$, both encoded by alternative reading frames of Arf/Ink4a locus, are known to induce the expression of p53 and Rb, respectively. By reducing the expression of both $p16^{Ink4a}$ and $p19^{Arf}$, iPS cell formation was increased relative to that attained by reducing the expression of $p19^{Arf}$ alone (Nature, 460, 1140-1144, 2009).

Polycomb group (PcG) proteins are epigenetic gene silencers. Bmi1, one of the PcG proteins, is involved in the down-regulation of both $p16^{Ink4a}$ and $p19^{Arf}$, which leads to suppressing the expression of p53 and Rb (Genes Dev, 2678-2690, 1999). Further, Bmi1 is known to regulate the expression of target genes by modifying chromatin organization. Thanks to these functions, Bmi1 plays an important role in the self-renewal of neural stem cells and hematopoietic stem cells. Based on this, the present inventors succeeded in the reprogramming of astrocytes to induce neural stem cells by overexpressing Bmi1 therein. The induced neural stem cells were similar in many aspects to those isolated from mice. Inter alia, the induced neural stem cells were found to have an increased expression level of Sox2, a gene essential for the self renewal of neural stem cells as one of reprogramming inducing genes (Biochem Biophys Res Commun. 371, 267-272, 2008).

Somatic cells require four (Oct4, Sox2, Klf4, C-Myc) or three (Oct4, Sox2, Klf4) genes for their dedifferentiation. It is known that these genes may not be additionally introduced into cells which endogenously express them. It was representatively demonstrated that the introduction of Oct4 alone induces the generation of iPS cells from mouse/human neural stem cells since they show the endogenous expression of Sox2, Klf4 and C-Myc (Nature, 461, 649-653, 2009).

It is reported that the addition of both the MEK inhibitor PD0325901 and the GSK3β inhibitor CHIR99021 can induce the differentiation of pre-iPS cells, which are in an intermediate state of the dedifferentiation process into fully reprogrammed cells (PLoS One, 6, 2237-2247, 2008).

In addition, the use of a G9a HMTase inhibitor and a DMNT inhibitor in a dedifferentiation process is known to increase the efficiency of reprogramming (Cell Stem Cell, 3, 568-574, 2008).

The efficiency of reprogramming can also be improved by treating with a histone deacetylase inhibitor (VPA) as part of a differentiation process (Cell Stem Cell, 4, 301-312, 2009).

Nowhere has, however, the induction of dedifferentiation by introducing a Bmi1 gene and treating with a low molecular weight substance and a method for generating pluripotent embryonic stem cell-like cells been known in the art.

SUMMARY OF THE INVENTION

The present inventors found that the introduction of mouse somatic cells to differentiate into epiblast stem cell-like cells could be achieved by Oct4 overexpression in combination with Bmi1 overexpression which results in the induction of Sox2 and the down-regulation of p16$^{Ink4a}$ and p19$^{Arf}$, and by control of the culture conditions. In this context, the identification of the formed cells as stem cell-like cells was achieved by selection with GFP from cells into which Oct4 promoter GFP was introduced. The cells thus formed, however, exhibited traits similar to those of pre-iPS. When these cells were treated with the low molecular weight substances PD0325901 and CHIR99021, and cultured in the culture conditions of mouse stem cells, they were shown to further dedifferentiate into iPS cells showing embryonic stem cell traits.

It was also found that treatment with the low molecular weight substances BIX02194 (G9a histone methyltransferase (G9a HMTase) inhibitor) and RG108 (DNA methyltransferase (DMNT) inhibitor) in combination or with VPA (Valporic Acid, histone deacetylase inhibitor) and a mouse embryonic stem cell culture condition induced Bmi1-transduced mouse cells to dedifferentiate into stem cell lines having traits similar to those of embryonic stem cells.

On the basis of these findings, Bmi1-transduced cells were treated with low molecular weight substances and cultured in the conditions used for embryonic stem cells. As a consequence, cell lines resembling embryonic stem cells were established. It was found that there was a high similarity in various properties including gene expression, epigenetics, and teratoma formation between the established cell lines and mouse embryonic stem cells.

It is therefore an object of the present subject matter to provide a composition for reprogramming somatic cells to generate embryonic stem cell-like cells, comprising a Bmi1 gene and at least one low molecular weight substance selected from among a set of a MEK inhibitor and a GSK inhibitor, a set of a G9a HMTase inhibitor and a DMNT inhibitor, and a histone deacetylase inhibitor (VPA).

It is another object of the present subject matter to provide a method for reprogramming somatic cells to generate induced pluripotent stem cells showing embryonic stem cell traits, using a Bmi1 gene and a low molecular weight substance.

It is a further object of the present subject matter to provide embryonic stem cell-like cells established by the method.

BRIEF DESCRIPTION OF THE DRAWINGS

The above and other objects, features and other advantages of the present subject matter will be more clearly understood from the following detailed description taken in conjunction with the accompanying drawings, in which:

FIG. 1A is of microphotographs showing the morphological change of Bmi1-transduced mouse somatic cells into germ cell-like cells with time under a specific culture condition;

FIG. 1B is a photographs of RT-PCR showing the same gene expression pattern of the Bmi1-transduced mouse somatic cells cultured in a specific condition as that of germ cell-like cells;

FIG. 2A is of fluorescence microphotographs showing iPS cells established by culturing Bmi1-transduced mouse somatic cells under specific conditions to produce epiblast stem cell-like cells, introducing an Oct4 promoter GFP into the cells to select Oct4-positive cells, treating the Oct4-positive cells with 0.5 μM PD0325901 and 3 μM CHIR99021, and culturing them in a condition used for embryonic stem cells (the established cells are named BC-iPS①);

FIG. 2B shows the expression of embryonic stem cell-specific markers in the iPS cells established by treatment with PD0325901 and CHIR99021, as detected by immunochemical staining. AP-positive colonies are detected by AP staining;

FIG. 2C shows the expression of the genes characteristic of embryonic stem cells in the iPS cells established by treatment with PD0325901 and CHIR99021, as measured by Western blotting analysis;

DESCRIPTION OF THE PREFERRED EMBODIMENTS

Figure 1A:
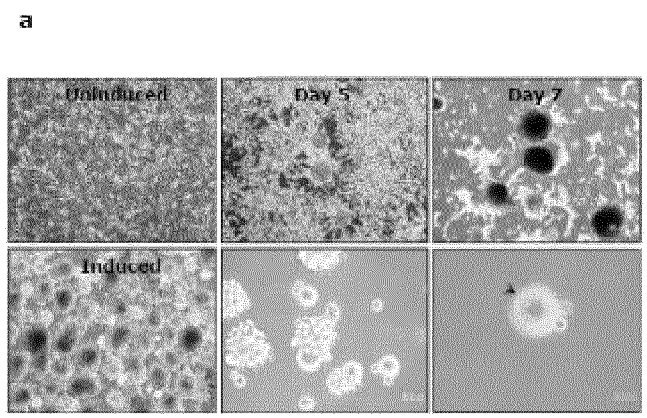
FIGS. 1A and 1B show the transformation of Bmi1-transduced mouse somatic cells into germ cell-like cells under specific culture conditions.

According to the present subject matter, Bmi1-transduced mouse somatic stem cells were cultured under specific conditions to produce epiblast stem cell-like cells into which an Oct4-promoter GFP was then introduced to select Oct4-positve cells. These cells were found to dedifferentiate into pluripotent embryonic stem cell-like cells when they were treated with low molecular weight substances (e.g., a set of PD0325901 and CHIR99021) and cultured under conditions used for embryonic stem cells.

Also, the present inventors found that epiblast stem cell-like cells formed by culturing Bmi1-transduced mouse somatic cells under specific conditions could be induced to dedifferentiate into pluripotent embryonic stem cell-like cells when they are treated with low molecular weight substances (e.g., a set of G9a HMTase inhibitor and DMNT inhibitor, or VPA alone) and cultured under conditions used for embryonic stem cells.

In accordance with an aspect thereof, the present subject matter provides a composition for reprogramming somatic cells to generate embryonic stem cells-like cells, comprising: a) a Bmi1 (B cell-specific Moloney murine leukemia virus integration site 1) protein or a nucleic acid molecule encoding the Bmi1 protein; and b) at least one low molecular weight substance selected from the group consisting of a set of a MEK/ERK (mitogen-activated protein kinase/extracellular regulated kinase) inhibitor and a GSK (glycogen synthase kinase) inhibitor, a set of a G9a HMTase inhibitor (G9a histone methyltransferase inhibitor) and a DMNT inhibitor (DNA methyltransferase inhibitor), and a histone deacetylase inhibitor.

In accordance with another aspect thereof, the present subject matter provides a method for reprogramming somatic cells to generate embryonic stem cell-like cells, comprising i) introducing a Bmi1 (B cell-specific Moloney murine leukemia virus integration site 1) protein or a nucleic acid molecule encoding the Bmi1 protein into the somatic cells; ii) culturing the Bmi1-transduced somatic cells under a condition used to culture neural stem cells; and iii) treating the cells with at least one low molecular weight substance selected from the group consisting of a set of a MEK/ERK (mitogen-activated protein kinase/extracellular regulated kinase) inhibitor and a GSK glycogen synthase kinase) inhibitor, a set of a G9a HMTase (histone methyltransferase) inhibitor and a DMNT (DNA methyltransferase) inhibitor, and a histone deacetylase inhibitor.

In step ii), the somatic cells are cultured for seven days or longer. Only after culturing for seven days or longer do the cells exhibit an expression pattern similar to that of the genes characteristic of embryonic stem cells, and can their differentiation efficiency be improved upon use in cell therapy.

According to an embodiment of the present subject matter, the method may further comprise culturing the cells under the culture conditions of embryonic stem cells. The culture conditions for embryonic stem cells include any medium typically used to culture embryonic stem cells. In an embodiment of the present subject matter, the Bmi1-transduced cells are cultured in a high-glucose DMEM supplemented with 15% FBS (Fetal bovine serum)+1% nonessential amino acid+1% penicillin/streptomycin+0.1 mM β-mercaptoethanol+1000 unit/ml mouse LIF (leukemia inhibitory factor) in the presence of feeder cells, with passage every two or three days.

As used herein, the term "embryonic stem cell (ESC)-like cell" is intended to refer to a pluripotent cell characterized by the properties of ESC including, but not being limited to, proliferation without transformation, infinite replication, self-renewal and differentiation into all three germ layers. In this context, the embryonic stem cell-like cells are used interchangeably with embryonic stem cells or induced pluripotent stem cells.

When inducing the generation of embryonic stem cell-like cells, no special limitations are imparted to the starting somatic cells. As long as it may be induced to undergo dedifferentiation, any somatic cell may be employed. For example, somatic cells in the embryonic period or matured somatic cells may be employed. When the embryonic stem cell-like cells are applied to the treatment of diseases, it is desirable that they be derived from somatic cells of the patients, e.g., somatic cells related to diseases or involved in disease treatment. Preferably, the somatic cells are fibroblasts which may be isolated from animals, preferably mammals, including humans, mice, horses, sheep, pigs, goats, camels, antelopes, dogs, etc.

Before use in reprogramming, fibroblasts are cultured in a medium. This medium may be any that is usually used for culturing fibroblasts. Typically, the medium contains a carbon source, a nitrogen source, and trace elements. In a preferred embodiment of the present subject matter, fibroblasts are cultured in DMEM (high glucose, w/o sodium pyruvate) supplemented with 10% FBS (Fetal bovine serum), 0.1 mM non-essential amino acid, 1% penicillin/streptomycin and 0.1 mM β-mercaptoethanol.

In accordance with an embodiment of the present subject matter Bmi1 may be in the form of a protein or a nucleic acid molecule encoding the Bmi1 protein. Examples of the Bmi1 useful in the present subject matter include those from animals including humans, horses, sheep, pigs, goats, camels, antelopes, dogs etc., with a preference for human Bmi1. In addition, Bmi1 proteins useful for dedifferentiation into embryonic stem cell-like cells may have its own wild-type amino acid sequence or variants thereof.

The Bmi1 protein variants refer to proteins which are different in amino acid sequence from wild-type proteins as a result of deletion, insertion, non-conservative or conservative substitution or a combination thereof at one or more amino acid residues while remaining biologically and functionally equivalent thereto with or without modification of the physicochemical properties. If modified, the variants may have increased structural stability in the face of physical and chemical conditions as well as increased physiological activity.

Preferably, Bmi1 is provided as a nucleotide sequence encoding the Bmi1 protein.

The nucleotide sequence may encode a wild-type protein of Bmi1 or a variant protein thereof which is modified, as mentioned above, at one or more nucleotide residues by substitution, deletion, insertion or a combination thereof. It may be isolated from nature or chemically synthesized.

The nucleotide sequence encoding the Bmi1 protein may be a DNA molecule (genomic DNA, cDNA) or an RNA molecule in the form of single- or double-strands.

In the present subject matter, the nucleotide sequence encoding the Bmi1 protein may be introduced into host cells using a technique well known in the art, such as in the form of naked DNA vector (Wolff et al. Science, 1990: Wolff et al., J Cell Sci. 103:1249-59, 1992), or with the aid of liposomes or cataionic polymers. A liposome is a phospholipid membrane for gene transfer, composed of a mixture of cationic phospholipids such as DOTMA and DOTAP. A liposomal complex which is suitable for gene transfer across the cell membrane is formed when cationic liposomes are mixed with anionic nucleic acid molecules in a certain ratio.

The term "vector", as used herein, refers to a DNA construct in which a gene of interest is operably linked to a regulatory element so that the gene can be expressed in a proper host which anchors the vector therein.

As used herein, the term "operably linked" refers to a functional linkage between a regulatory element and a nucleotide sequence encoding a protein of interest in such a functional relationship that the element can serve to initiate and mediate the transcription of the nucleotide sequence. In a recombinant vector, the functional linkage may be obtained using a genetic recombination technique well known in the art. Site-specific DNA cleavage and linkage may be accomplished with typical enzymes.

The regulator element of the vector useful in the present subject matter may include a signal or leader sequence for a membrane targeting or secreting as well as expression regulatory elements such as a promoter, an operator, an initiation codon, a stop codon, a polyadenylation signal and an enhancer, depending on the purpose thereof. The promoter may be constitutive or inducible. Moreover, the expression vector may contain a selection marker for selecting host cells transformed therewith. If replicable, the expression vector will contain a replication origin. The vector may be self-replicable or may be integrated into the chromosome of the host cell.

Plasmids, cosmids, and viral vectors may fall within the scope of the vectors useful in the present subject matter. Preferable are viral vectors. Examples of the viral vectors include, but are not limited to, those derived from retrovirus, such as HIV (Human immunodeficiency virus) MLV (Murineleukemia virus) ASLV (Avian sarcoma/leukosis), SNV (Spleen necrosis virus), RSV (Rous sarcoma virus), MMTV (Mouse mammary tumor virus), etc., adenovirus, adeno-associated virus, and herpes simplex virus. In an embodiment of the present subject matter, a Bmi1 gene is inserted into a pBabe puro vector, that is, MLV (Moloney leukemia virus)-based virus vector with a selection marker for puronmycin.

In an embodiment of the present subject matter, a recombinant vector (pBabe puro Bmi1) constructed by inserting a nucleotide sequence (NCBI accession No. L13689) encoding a Bmi1 protein into a pBabe puro vector is transfected into PT packaging cell line to produce viruses expressing Bmi1 which are then used to infect fibroblasts. Viruses packaged from PT67 cells show high viral titers and can be used to infect a broad range of mammalian cells.

In a preferred embodiment of the present subject matter, the method for reprogramming somatic cells to generate embryonic stem cell-like cells comprises i) introducing a Bmi1 (B cell-specific Moloney murine leukemia virus integration site 1) protein or a nucleic acid molecule encoding the Bmi1 protein into the somatic cells; ii) culturing the somatic cell in the presence of bFGF (basic Fibroblast Growth Factor) under conditions used for neural stem cells; iii) selecting cells expressing Oct4 and iv) treating the cells with a set of a MEK/ERK inhibitor and a GSK inhibitor.

Figure 1B:
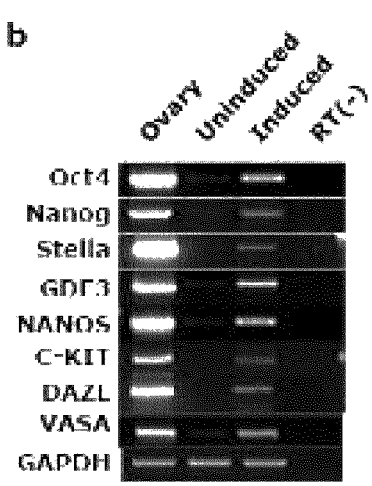

In the method, any medium that is typically used to culture neural stem cells may be included in the conditions used for neural stem cells in step (ii) if it contains bFGF (basic Fibroblast Growth Factor) therein. A preferable medium does not contain EGF (Epidermal Growth Factor), but bFGF alone. In a preferred embodiment of the present subject matter, DMEM/F12+B27+N2+1% penicillin/streptomycin+20 ng/ml bFGF was used as a neural stem cell-culturing condition. When cultured under these conditions, the somatic cell is transformed into germ cell-like cells (FIGS. 1A and 1B).

Selection of the cells expressing Oct4 as in step iii) provides the advantage of further increasing the differentiation efficiency when the embryonic stem cell-like cells are used in cell therapy. The cells expressing Oct4 can be selected using various well-known methods. In an embodiment of the present subject matter, Oct4-positive dedifferentiated stem cells were established by selecting GFP-expressing cells after the introduction of Oct4-(p)-GFP (Nature 448, 318-324).

The term "MEK/ERK inhibitor" used in step iv) refers to a substance targeting ERK1/2 and its upstream molecule MEK1/2, both involved in the MEK/ERK (mitogen-activated protein kinase/extracellular regulated kinase) signaling pathway.

MEK (mitogen-activated protein kinase) is an enzyme which acts at the end of the MAP kinase signaling pathway, serving as a mediator for transmitting extracellular signals into the nucleus. The enzyme specifically phosphorylates threonine (Thr) residues of the myelin basic protein in vitro. ERK is a typical MAP kinase present in higher organisms, which functions to phosphorylate threonine (Thr) and tyrosine (Tyr) residues in response to extracellular signals. It is reported that because the phosphorylation of threonine and tyrosine residues plays a crucial role in the activation of MAP kinase, the enzyme is not activated when these resides are substituted with different amino acid residues.

Preferably, the MEK/ERK inhibitor contained in the composition of the present subject matter means PD0325901 or U0126. U0126 has the IUPAC name of 1,4-diamino-2,3-dicyano-1,4-bis[2-aminophenylthio] butadiene. It is apparent to those skilled in the art that all inhibitors against the MKE/ERK signaling pathway, inclusive of the compounds, fall within the scope of the present subject matter. ERK 1/2 is activated by MEK 1/2 and can be deactivated by regulating MEK 1/2. Thus, MEK 1/2 is a signaling molecule directly upstream of ERK1/2.

As used herein, the term "GSK inhibitor" is intended to refer to a substance targeting GSK1/2, which is an upstream molecule of the GSK (glycogen synthase kinase) signaling pathway. In the present subject matter, GSK preferably means GSK3β. The GSK inhibitor contained in the composition of the present subject matter is preferably CHIR99021, an aminopyrimidine. It is, however, apparent to those skilled in the art that all GSK inhibitors including the aminopyrimidine fall within the scope of the present subject matter.

The low molecular weight substances including the MEK/ERK inhibitors and the GSK inhibitors may be commercially available or may be chemically synthesized. Treatment with the inhibitors induces pre-iPS cells to dedifferentiate into fully reprogrammed cells (PLoS One, 6, 2237-2247).

The MEK/ERK inhibitors and the GSK inhibitor may be added to a culture medium. The culture medium contains the inhibitors at effective concentrations which may vary depending on well-known factors including the kind of medium, culturing methods, etc. In an embodiment of the present subject matter, the culture medium contains PD0325901 at a concentration of 0.5 µM and CHIR99021 at a concentration of 3 µM.

In accordance with a preferred embodiment thereof, the present subject matter provides a method for reprogramming somatic cells to generate embryonic stem cell-like cells, comprising: i) introducing a Bmi1 (B cell-specific Moloney murine leukemia virus integration site 1) protein or a nucleic acid molecule encoding the Bmi1 protein into the somatic cells; ii) culturing the somatic cell in the presence of bFGF (basic Fibroblast Growth Factor) under conditions used for neural stem cells; iii) treating the cells with a set of a G9a HMTase inhibitor and a DMNT inhibitor.

The term G9a HMTase inhibitor used in step iii) refers to a substance functioning to interfere with the function of G9a histone methyltransferase and to promote the generation of H3K9me2.

G9a HMTase (G9a histone methyltransferase) is an enzyme which induces methylation at lysine with specific selectivity for the lysine residues of histone and contains a SET (Suvar3-9, Enhancer-of-zeste, Trithorax) domain showing specific enzyme activity.

Preferably, the G9a HMTase inhibitor used in the composition of the present subject matter may be BIX01294, which has an IUPAC name of 2-(Hexahydro-4-methyl-1H-1,4-diazepin-1-yl)-6,7-dimethoxy-N-[1-(phenylmethyl)-4-piperidinyl]4-quinazolinamine. However, it should be understood to those skilled in the art that any other G9a HMTase inhibitor in addition to this compound falls within the scope of the present subject matter.

As used herein, the term "DMNT inhibitor" refers to a substance inhibiting the activity of DMNT (DNA methyltransferase). Preferably, the DMNT inhibitor used in the composition of the present subject matter may be RG108, which has the IUPAC name of N-Phthalyl-L-tryptophan. It should be however understood to those skilled in the art that any other DMNT inhibitors in addition to the compound fall within the scope of the present subject matter.

The low molecular weight substances including the G9a HMTase inhibitor and the DMNT inhibitor may be commercially available (Stemolecule™) or may be chemically synthesized. Treatment with these inhibitors improves dedifferentiation efficiency (Cell Stem Cell, 3, 568-574, 2008).

The G9a HMTase inhibitor and the DMNT inhibitor may be added to a culture medium. The culture medium contains the inhibitors at effective concentrations which may vary depending on well-known factors including the kind of medium, culturing methods, etc. In an embodiment of the present subject matter, the culture medium contains BIX01294 at a concentration of 1 µM and RG108 at a concentration of 0.5 µM.

In accordance with a preferred embodiment thereof, the present subject matter provides a method for reprogramming somatic cells to generate embryonic stem cell-like cells, comprising: i) introducing a Bmi1 (B cell-specific Moloney murine leukemia virus integration site 1) protein or a nucleic acid molecule encoding the Bmi1 protein into the somatic cells; ii) culturing the somatic cell under conditions used for neural stem cells; iii) treating the cells with a histone deacetylase inhibitor.

In the method, any medium that is typically used to culture neural stem cells may be included in the conditions used for neural stem cells in step (ii). In a preferred embodiment of the present subject matter, DMEM/F12+B27+N2+1% penicillin/streptomycin+20 ng/ml bFGF+20 ng/ml EGF was used as a neural stem cell-culturing condition. When cultured in this condition, the somatic cell is transformed into a neural stem cell.

The histone deacetylase inhibitor used in step iii) means a substance that interferes with the function of histone deacetylase. Histone deacetylase inhibition induces the accumulation of hyperacetylated nucleosome core histones in most regions of chromatin, which leads to the up-regulation of cytostatic factors and some genes essential for differentiation. That is, the histone deacetylase inhibitor is a cytostatic agent that inhibits the proliferation of tumor cells by inducing cell cycle arrest at the G1 phase, differentiation and apoptosis of tumor cells and repressing angiogenesis.

Histone deacetylase (HDAC) functions to suppress gene transcription by the mediation of pRB/E2F. Inhibition of histone acetylation is correlated with the onset of various cancers. HDAC, which is induced to be overexpressed under specific environmental conditions such as hypoxia, hypoglycemia, cellular tumorigenesis, etc., down-regulates cytostatic factors, leading to cell proliferation. HDAC is known to serve as an important factor in cellular tumorigenesis and differentiation regulation.

Among the histone deacetylase (HDAC) inhibitors useful in the present subject matter are VPA (valproic acid, 2-propylenepentanoic acid), trichostatin (TSA) and derivatives thereof, VPA being preferred.

VPA is known to deplete inositol, inhibit GSK-3β, activate ERK pathway and stimulate PPAR activity. Trichostatin is a histone deacetylase inhibitor derived from Streptomyces. Not only trichostatin, but also its derivatives showing inhibitory activity against HDAC in vitro or in vivo are included within the scope of the present subject matter. In addition, various inorganic salts and organic salts of the trichostatin derivatives, if pharmaceutically acceptable, may used in the present subject matter. In the composition of the present subject matter, trichostatin or its derivative may be contained at a concentration of from 300 to 900 µM and preferably at a concentration of from 500 to 800. Too low a concentration cannot bring about the desired effect. On the other hand, if the concentration is too high, the composition becomes toxic to cells. Thus, proper concentrations must be determined according to cell types.

It should be appreciated that any other histone deacetylase inhibitors besides the compounds are within the scope of the present subject matter.

The low molecular weight substances including histone deacetylase inhibitors may be commercially available (Stemolecule™) or may be chemically synthesized. Treatment with these inhibitors improves dedifferentiation efficiency (Cell Stem Cell, 4, 301-312, 2009).

The histone deacetylase inhibitor may be added to a culture medium. The culture medium contains the inhibitor at effective concentrations which may vary depending on well-known factors including the kind of medium, culturing methods, etc. In an embodiment of the present subject matter, the culture medium contains VPA at a concentration of 0.5 µM.

In accordance with still another aspect thereof, the present subject matter provides an embryonic stem cell-like cell prepared by the method.

The embryonic stem cell-like cell prepared by the reprogramming method of present invention was found to exhibit the same pluripotency as typical embryonic stem cells in terms of gene expression, epigenetics, in-vitro and in-vivo differentiation into all three germ layers, teratoma formation and chimeric mouse generation.

The embryonic stem cell-like cells of the present subject matter are a wonderful source for various types of cells. For example, when cultured under conditions used for cell differentiation, the embryonic stem cell-like cells may be induced to differentiate into hematopoietic cells, neurons, beta cells, hepatocytes, chondrocytes, epithelial cells, urothelial cells, and analog cells thereof.

As to conditions, media and methods for the differentiation of embryonic stem cell-like cells, reference may be made to Palacios, et al., PNAS. USA, 92:7530-7537 (1995), Pedersen, J. Reprod. Fertil. Dev., 6; 543-552 (1994), and Bain et al., Dev. Biol, 168:342-357 (1995). By means of implantation, the embryonic stem cell-like cells may be applied to the treatment of a number of diseases including diabetes mellitus, Parkinson's disease, Alzheimer's disease, cancer, spinal cord injury, multiple sclerosis, amyotrophic lateral sclerosis (Lou Gehrig's disease), muscular dystrophy, hepatic diseases, hypercholesterolemia, cardiac diseases, cartilage diseases, wounds, foot ulcer, gastroenteric disorders, vascular diseases, renal diseases, uterine diseases, senescence-related diseases, etc. Besides, the embryonic stem cell-like cells of the present subject matter may be useful for the evaluation of drugs.

A better understanding of the present subject matter may be obtained through the following examples which are set forth to illustrate, but are not to be construed as limiting, the present subject matter.

EXAMPLE 1

Culture of Mouse Somatic Cells and Introduction of Bmi1 Gene Thereinto

Mouse somatic cells, in detail, mouse fibroblasts were employed to generate embryonic stem cell-like cells. Embryos were taken from CF1 strain mice on embryonic day 13.5. Cells were cultured in DMEM (high glucose, w/o sodium pyruvate) supplemented with 10% FBS (Fetal bovine serum), 0.1 mM non-essential amino acid, 1% penicillin/streptomycin and 0.1 mM β-mercaptoethanol in tissue culture flasks, after which fibroblasts at the $3^{rd}$ passage were seeded at a density of $2 \times 10^5$ cells/well into 6-well plates.

For use in gene transfer, retrovirus particles were prepared from the PT67 packaging cell line. In this context, a pBabe puro Bmi1 (from Dr. G. P. Dimri, Evanston Northwestern Healthcare Research Institute, Feinberg School of Medicine, Northwestern University, Evanston, Ill. 60201, USA), constructed by inserting a human Bmi1 gene (NCBI accession No. L13689) into a pBabe puro vector, was transfected into a PT67 packaging cell line (Clontech) with the aid of Turbofect (Fermentas), followed by drug selection with puromycine (3 µg/ml, BD bioscience). The PT67 packaging cell line allowed the production of high-titer viruses capable of infecting a broad range of mammalian host cells.

The expression of each gene was monitored with RT-PCR. When the cells were grown to 80% confluency, the supernatant was taken, filtered through a 0.45 µm filter (Millipore) to remove cell debris, and added to the cells in the presence of polybrene (6 µg/ml, sigma). The infection was repeated three times at regular intervals of 12 hrs.

EXAMPLE 2

Reprogramming of Bmi1-Transduced Somatic Cells into Germ Cell-Like Cells Under Specific Culture Condition When cultured in an EGF-free condition for neural stem cells (DMEM/F12+B27+N2+1% penicillin/streptomycin+ 20 ng/ml bFGF), mouse somatic cells into which a Bmi1 gene was introduced with a retrovirus were reprogrammed to form cells similar to neurospheres which then progressed to form germ cell-like cells (FIG. 1A). These cells were found to express the genes of germ cells as analyzed by RT-PCR (FIG. 1B).

EXAMPLE 3

Selection of Oct4-Positive Cells Using Oct4-Promoter-GFP, Reprogramming into iPS Cells by Treatment with Low Molecular Weight Substances PD0325901 and CHIR99021, and Characterization of Embryonic Stem Cells 1) Selection of Oct4-Positive Cells Using Oct4-Promoter-GFP To compensate for the fact that the dedifferentiated stem cells established in Example 2 were observed to not form chimeras, Oct4-®-GFP (refer to Nature 448, 318-324) was introduced, followed by selecting Oct4-positive cells with GFP.

The selected cells were able to progress further to cells capable of chimera formation. However, they could not be regarded as fully reprogrammed cells because they differed from embryonic stem cells in gene expression.

2) Reprogramming into iPS Cells by Treatment with Low Molecular Weight Substances PD0325901 and CHIR99021

The Oct4-positive cells were treated with 0.5 μM PD0325901 and 3 μM CHIR99021 and induced to undergo reprogramming under the culture conditions of mouse embryonic stem cells to establish induced stem cells, called BC-iPS①. The conditions of mouse embryonic stem cells were such that the cells were cultured in a high-glucose DMEM supplemented with 15% FBS (Fetal bovine serum)+1% nonessential amino acid+1% penicillin/streptomycin+β-mercaptoethanol+1000 unit/ml mouse LIF (leukemia inhibitory factor) in the presence of feeder cells, with a passage every two or three days.

3) Characterization of Embryonic Stem Cells

Figure 2A:
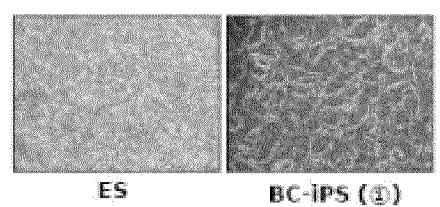
FIGS. 2A-2C show the effect of the low molecular weight substances PD0325901 and CHIR99021 on the reprogramming of Bmi1-transduced mouse somatic cells to generate iPS cells.

The cells treated with the low molecular weight substances were transferred onto feeder cells and cultured to form colonies. The established iPS cells were observed to have morphology similar to that of embryonic stem cells, as shown in FIG. 2A.

Figure 2B:
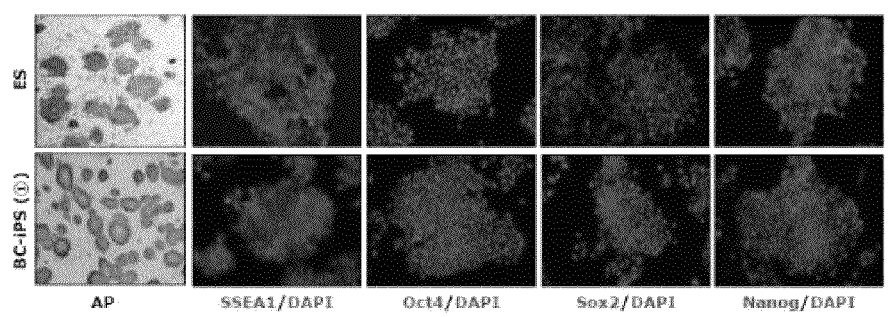

The reprogrammed cells were observed to be positive to AP as measured by AP staining and to express markers characteristic of embryonic stem cells, as measured by immunochemical staining (FIG. 2B)

Figure 2C:
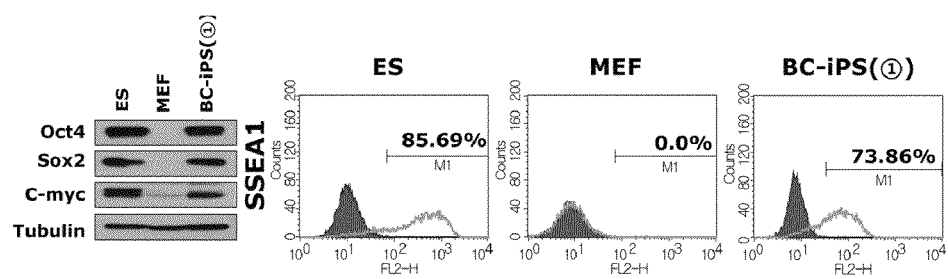

Also, hallmark genes of embryonic stem cells were expressed in the reprogrammed cells as analyzed by Western blotting. FACS analysis showed the expression of SSEA1, a representative indicator of embryonic stem cells (FIG. 2C). As is apparent from this data, the introduction of Bmi1 gene and the treatment with the low molecular weight substances can induce somatic stem cells to dedifferentiate into embryonic stem cell-like cells.

Figure 3:
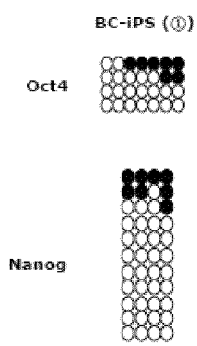
FIG. 3 shows the demethylation of the promoter regions of Oct4 and Nanog, both involved in the self-renewal of embryonic stem cells, in the iPS cells established by treatment with PD0325901 and CHIR99021.

4) Assay of Promoters of Main Genes for Methylation in iPS Cells and Embryonic Stem Cells Promoters of the genes essential for the self-renewal of embryonic stem cells were assayed in induced stem cells. In this regard, bisulfate sequencing was performed to examine the methylation status of Oct4 and Nanog promoter regions. They were, for the most part, methylated in mouse somatic cells, but demethylated in the induced stem cells like embryonic stem cells (FIG. 3), indicating that the cells established by the reprogramming process have the same properties as do embryonic stem cells.

5) Assay of Differentiation Potential of Induced Stem Cells

Figure 4:
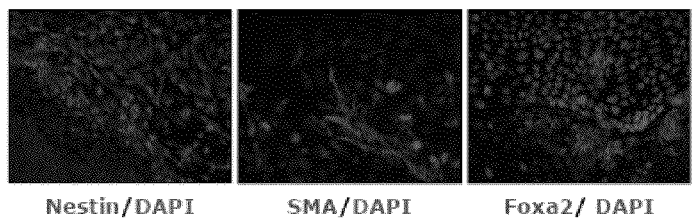
FIG. 4 shows the spontaneous differentiation of the embryonic bodies of the iPS cells established by treatment with PD0325901 and CHIR99021 into respective cells representative of the three germ layers.

The differentiation potential of the induced stem cells was examined in vitro. Embryonic bodies (EB) were seeded onto 0.1% gelatin-coated plates and allowed to undergo spontaneous differentiation for seven days in EB media. The EB was found to express the genes characteristic of the three germ layers. An immunochemical staining assay detected typical markers, demonstrating in vitro differentiation into the three germ cells (FIG. 4).

Figure 5:
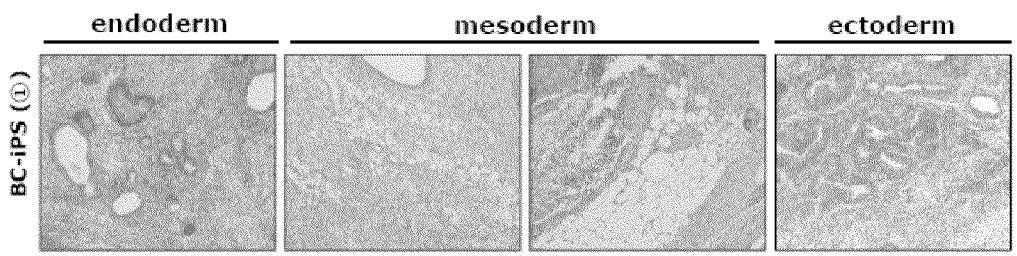
FIG. 5 shows the induction of in vivo differentiation into all three germ layers in terms of the teratoma formation in the iPS cells established by treatment with PD0325901 and CHIR99021 like embryonic stem cells. The iPS cells were injected under the kidney capsule into Balb/c nude mice, 8-10 weeks after which the mice developed teratomas which were prepared for H&E staining.

To investigate the differentiation potential of the iPS cells in vivo, they were assayed for teratoma formation. 1×10⁶ cells were centrifuged at 8000 rpm for 5 min and the pellet thus obtained was cultured for 24 hrs in a proliferation medium for embryonic stem cells, followed by injecting the cells under the kidney capsule into the dorsal flank of 6-week-old Balb/c nude mice. Eight to ten weeks later, the kidney was excised, embedded in paraffin, and processed for H&E staining. The results showed differentiation of the iPS cells into cells corresponding to the three germ lines, confirming the teratoma formation thereof (FIG. 5). These results demonstrated that the iPS cells have properties similar to those of embryonic stem cells.

EXAMPLE 4

Reprogramming into iPS Cells by Treatment with Low Molecular Weight Substances BIX01294 and RG108, and Characterization of Embryonic Stem Cells 1) Reprogramming into iPS Cells by Treatment with Low Molecular Weight Substances When cultured in an EGF-free condition for neural stem cells (DMEM/F12+B27+N2+1% penicillin/streptomycin+20 ng/ml bFGF), Bmi1-transduced mouse somatic cells were reprogrammed to form cells similar to neurospheres which were then treated with the low molecular weight substances BIX01294 and RG108. In greater detail, the neurosphere-like cells were seeded as single cells onto 0.1% gelatin coated plates and incubated for one week with 1 μM BIX01294 and 0.5 μM RG108 under a condition used for mouse embryonic stem cells to establish iPS cells which were named BC-iPS②. As for the conditions used for mouse embryonic stem cells, the cells were cultured in a high-glucose DMEM supplemented with 15% FBS (Fetal bovine serum)+1% nonessential amino acid+1% penicillin/streptomycin+β-mercaptoethanol+1000 unit/ml mouse LIF (leukemia inhibitory factor) in the presence of feeder cells, with passage every two or three days.

2) Characterization of Embryonic Stem Cells

Figure 6A:
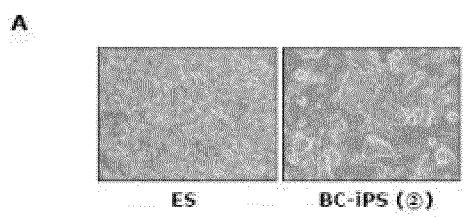
FIG. 6A is of fluorescence microphotographs showing embryonic stem cell-like cells established by culturing Bmi1-transduced mouse somatic cells under specific conditions to produce epiblast stem cell-like cells, treating the cells with BIX01294 and RG1080 and culturing them in a condition used for embryonic stem cells (the established cells are named BC-iPS②)

The cells treated with the low molecular weight substances were transferred onto feeder cells and cultured to form colonies. The established iPS cells were observed to have morphology similar to that of embryonic stem cells, as shown in FIG. 6A.

Figure 6B:
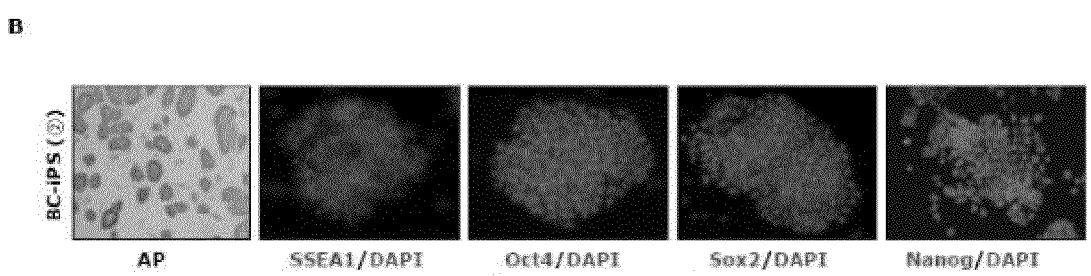
FIG. 6B shows the expression of embryonic stem cell-specific markers in the iPS cells established by treatment with BIX01294 and RG1080, as detected by immunochemical staining. AP-positive colonies are detected by AP staining.

The reprogrammed cells were observed to be positive to AP as measured by AP staining and to express markers characteristic of embryonic stem cells, as measured by immunostaining (FIG. 6B)

Figure 6C:
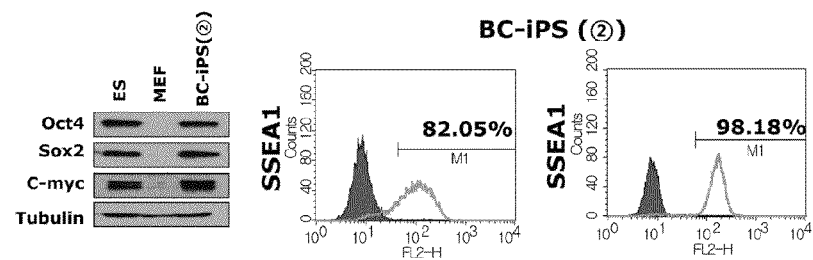
FIG. 6C shows the expression of the genes characteristic of embryonic stem cells in the iPS cells established by treatment with BIX01294 and RG1080, as measured by Western blotting analysis.

Also, hallmark genes of embryonic stem cells were expressed in the reprogrammed cells as analyzed by Western blotting. FACS analysis showed the expression of SSEA1, a representative indicator of embryonic stem cells (FIG. 6C). As is apparent from this data, the introduction of Bmi1 gene and the treatment with the low molecular weight substances can induce somatic stem cells to dedifferentiate into embryonic stem cell-like cells.

Figure 7:
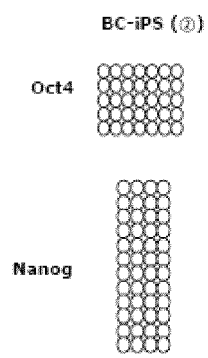
FIG. 7 shows the demethylation of the promoter regions of Oct4 and Nanog, both involved in the self-renewal of embryonic stem cells, in the iPS cells established by treatment with BIX01294 and RG1080.

3) Assay Methylation of Promoters of Main Genes in iPS Cells and Embryonic Stem Cells Promoters of the genes essential for the self-renewal of embryonic stem cells were assayed in induced stem cells. In this regard, bisulfate sequencing was performed to examine the methylation status of Oct4 and Nanog promoter regions. They were, for the most part, methylated in mouse somatic cells, but demethylated in the induced stem cells like embryonic stem cells (FIG. 7), indicating that the cells established by the reprogramming process have the same properties as do embryonic stem cells.

4) Assay of Differentiation Potential of Induced Stem Cells

Figure 8:
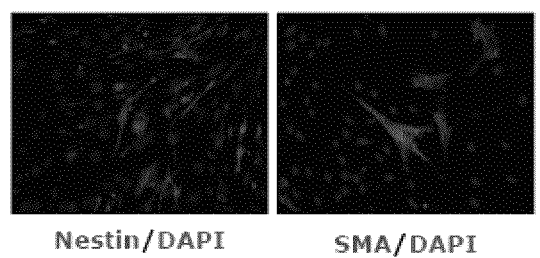
FIG. 8 shows the spontaneous differentiation of the embryonic bodies of the iPS cells established by treatment with BIX01294 and RG1080 into respective cells representative of the three germ layers.

The differentiation potential of the induced stem cells was examined in vitro. Embryonic bodies (EB) formed from the induced stem cells were seeded onto 0.1% gelatin-coated plates and allowed to undergo spontaneous differentiation for seven days in EB media. The EB was found to express the genes characteristic of the three germ layers. An immunochemical staining assay detected typical markers, demonstrating in vitro differentiation into the three germ cells (FIG. 8).

Figure 9:
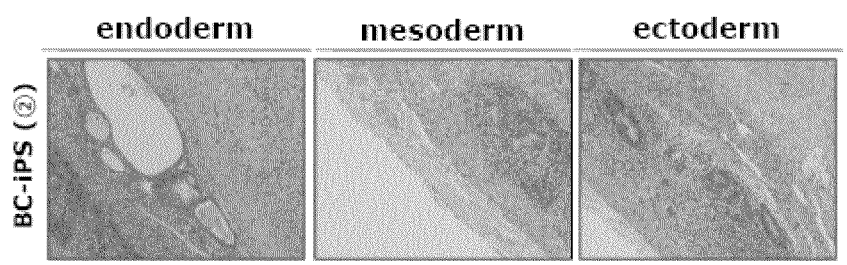
FIG. 9 shows the induction of in vivo differentiation into all three germ layers in terms of the teratoma formation in the iPS cells established by treatment with BIX01294 and RG1080 like embryonic stem cells. The iPS cells were injected under the kidney capsule into Balb/c nude mice, 8-10 weeks after which the mice developed teratomas which were prepared for H&E staining.

To investigate the differentiation potential of the iPS cells in vivo, they were assayed for teratoma formation. $1\times10^6$ cells were centrifuged at 8000 rpm for 5 min and the pellet thus obtained was cultured for 24 hrs in a proliferation medium for embryonic stem cells, followed by injecting the cells under the kidney capsule into the dorsal flank of 6-week-old Balb/c nude mice. Eight to ten weeks later, the kidney was excised, embedded in paraffin, and processed for H&E staining. The results showed differentiation of the iPS cells into cells corresponding to the three germ lines, confirming the teratoma formation thereof (FIG. 9). These results demonstrated that the iPS cells have properties similar to those of embryonic stem cells.

EXAMPLE 5

Reprogramming of Bmi1-Transduced Somatic Cells into Neural Stem Cell-Like Cells Under Specific Culture Condition When cultured in a condition used for neural stem cells (DMEM/F12+B27+N2+1% penicillin/streptomycin+20 ng/ml bFGF+20 ng/ml EGF), mouse somatic cells into which a Bmi1 gene was introduced by retrovirus were reprogrammed to form cells similar to neurospheres which were then progressed to neural stem cell-like cells. These cells were found to express the genes of neural stem cell-like cells as analyzed by RT-PCR.

EXAMPLE 6

Reprogramming into iPS Cells by Treatment with Low Molecular Weight Substance VPA (Valproic Acid), and Characterization of Embryonic Stem Cells 1) Reprogramming into iPS Cells by Treatment with VPA (Valproic Acid)

When cultured in a condition used for neural stem cells for one week, Bmi1-transduced mouse somatic cells were reprogrammed to form cells similar to neurospheres which were then treated with the low molecular weight substance VPA (valproic acid). In greater detail, the neurosphere-like cells were seeded as single cells onto 0.1% gelatin coated plates and incubated for one week with 2 mM VPA under a condition used for mouse embryonic stem cells. As for the conditions used for mouse embryonic stem cells, the cells were cultured in a high-glucose DMEM supplemented with 15% FBS (Fetal bovine serum)+1% nonessential amino acid+1% penicillin/streptomycin+β-mercaptoethanol+1000 unit/ml mouse LIF (leukemia inhibitory factor) in the presence of feeder cells, with passage every two or three days. As a result, iPS cells were established and named BC-iPS®.

2) Characterization of Embryonic Stem Cells

Figure 10A:
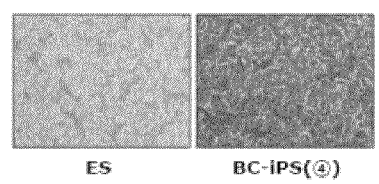
FIG. 10A is of fluorescence microphotographs showing embryonic stem cell-like cell established by culturing Bmi1-transduced mouse somatic cells in a specific condition to produce neurosphere-like cells, treating the cells with VPA and culturing them in a condition used for embryonic stem cells (the established cells are named BC-iPS④)

The cells treated with the low molecular weight substances were transferred onto feeder cells and cultured to form colonies. The established iPS cells were observed to have morphology similar to that of embryonic stem cells, as shown in FIG. 10A.

Figure 10B:
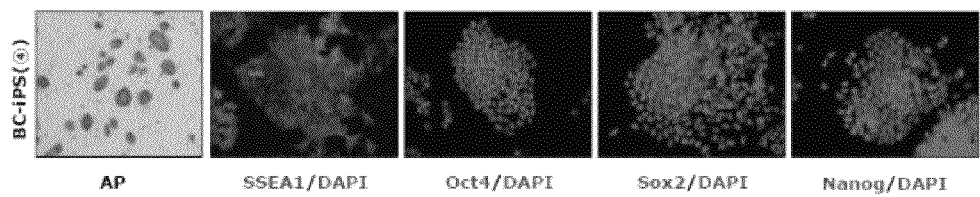
FIG. 10B shows the expression of embryonic stem cell-specific markers in the iPS cells established by treatment with VPA, as detected by immunochemical staining. AP-positive colonies are detected by AP staining.

The reprogrammed cells were observed to be positive to AP as measured by AP staining and to express markers characteristic of embryonic stem cells, as measured by immunochemical staining (FIG. 10B)

Figure 10C:
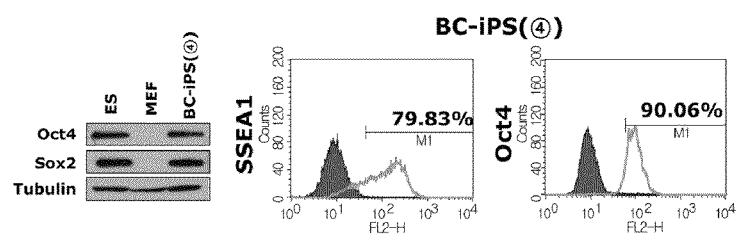
FIG. 10C shows the expression of the genes characteristic of embryonic stem cells in the iPS cells established by treatment with VPA, as measured by Western blotting analysis, and the expression of SSEA1 and Oct4 as measured by FASC.

Also, hallmark genes of embryonic stem cells were expressed in the reprogrammed cells as shown by Western blotting analysis. FACS analysis showed the expression of SSEA1 and Oct4, representative indicator and marker of embryonic stem cells (FIG. 10C). As is apparent from this data, the introduction of Bmi1 gene and the treatment with the low molecular weight substance can induce somatic stem cells to dedifferentiate into embryonic stem cell-like cells.

Figure 11:
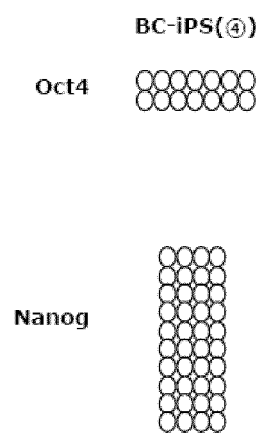
FIG. 11 shows the demethylation of the promoter regions of Oct4 and Nanog, both involved in the self-renewal of embryonic stem cells, in the iPS cells established by treatment with VPA.

3) Assay of Methylation of Promoters of Main Genes in iPS Cells and Embryonic Stem Cells Promoters of the genes essential for the self-renewal of embryonic stem cells were assayed in induced stem cells. In this regard, bisulfate sequencing was performed to examine the methylation status of Oct4 and Nanog promoter regions. They were, for the most part, methylated in mouse somatic cells, but demethylated in the induced stem cells like embryonic stem cells (FIG. 11), indicating that the cells established by the reprogramming process have the same properties as do embryonic stem cells.

4) Assay of Induced Stem Cells for Differentiation Potential

Figure 12:
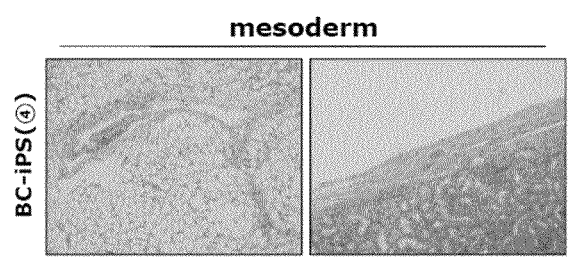
FIG. 12 shows the induction of in vivo differentiation into all three germ layers in terms of the teratoma formation in the iPS cells established by treatment with VPA, as in embryonic stem cells. The iPS cells were injected into Balb/c nude mice under the kidney capsule, 8-10 weeks after which the mice developed teratomas which were prepared for H&E staining.

To investigate the differentiation potential of the iPS cells in vivo, they were assayed for teratoma formation. $1\times10^6$ cells were centrifuged at 8000 rpm for 5 min and the pellet thus obtained was cultured for 24 hrs in a proliferation medium for embryonic stem cells, followed by injecting the cells under the kidney capsule into the dorsal flank of 6-week-old Balb/c nude mice. Eight to ten weeks later, the kidney was excised, embedded in paraffin, and processed for H&E staining. The results showed differentiation of the iPS cells into cells corresponding to the three germ lines, confirming the teratoma formation thereof (FIG. 12). These results demonstrated that the iPS cells have properties similar to those of embryonic stem cells.

As described hitherto, somatic cells can be induced to undergo dedifferentiation into pluripotent stem cells by the introduction of a Bmi1 in combination with treatment with at least one low molecular weight substance selected from among a set of a MEK/ERK inhibitor and a GSK inhibitor, a set of a G9a HMTase inhibitor and a DMNT inhibitor, and a histone deacetylase inhibitor, followed by culturing under the conditions used for embryonic stem cells. In suitable conditions, the induced embryonic stem cell-like cells prepared according to the present subject matter can differentiate into, for example, cardiomyocytes, insulin-producing cells, or neurons which are thus useful in cell therapy for various diseases including cardiac dysfunction, insulin-dependent diabetes, Parkinson's diseases, spinal cord injury, etc. Thus, the induced embryonic stem cell-like cells are promising solutions to the problems occurring with human embryos, that is, the death of the human embryo and immunological rejection. In addition, various cells (e.g., cardiomyocytes, hepatocytes, etc.) differentiated from the iPS cells are used as systems for evaluating chemicals, drugs, poisons, etc. for medicinal efficacy or toxicity.

Further, the present subject matter allows the generation of induced pluripotent stem cells by a method which can be conducted simply by introducing a Bmi1 gene alone and treating with a low molecular weight substance. Thus, the present subject matter provides a useful technique on the basis of which a method can be provided for generating iPS cells without introducing any gene.

Although the preferred embodiments of the present subject matter have been disclosed for illustrative purposes, those skilled in the art will appreciate that various modifications, additions and substitutions are possible, without departing from the scope and spirit of the invention as disclosed in the accompanying claims.

What is claimed is:

1. A method for reprogramming a somatic cell to produce pluripotent cells comprising:
    (i) transducing a somatic cell with a nucleic acid comprising the coding sequence for B cell-specific Moloney murine leukemia virus integration site 1 (Bmi-1) operably linked to a promoter, wherein said transducing results in overexpression of Bmi-1 protein in said somatic cell and produces a transduced somatic cell;
    (ii) culturing said transduced somatic cell in a medium comprising basic Fibroblast Growth Factor (bFGF) and is free of Epidermal Growth Factor (EGF), wherein said culturing produces neuro spheres;
    (iii) obtaining cells from said neurospheres; and
    (iv) culturing said cells obtained from said neuro spheres in the presence of a mitogen-activated protein kinase (MAP)/extracellular regulated kinase (ERK) inhibitor and a glycogen synthase kinase (GSK) inhibitor in an embryonic stem cell medium for a time sufficient to produce pluripotent cells from said cells obtained from said neurospheres, thereby reprogramming a somatic cell to produce induced pluripotent cells.

2. The method of claim 1, wherein the method further comprises a step of selecting Oct4-expressing cells after step (iii).

3. The method of claim 1, wherein the MAP/ERK inhibitor is PD0325901 and the GSK inhibitor is CHIR99021, which inhibits GSK3β.

4. A method for reprogramming a somatic cell to produce pluripotent cells comprising:
    (i) transducing a somatic cell with a nucleic acid comprising the coding sequence for B cell-specific Moloney murine leukemia virus integration site 1 (Bmi-1) operably linked to a promoter, wherein said transducing results in overexpression of Bmi-1 protein in said somatic cell and produces a transduced somatic cell;
    (ii) culturing said transduced somatic cell in a medium comprising basic Fibroblast Growth Factor (bFGF) and is free of Epidermal Growth Factor (EGF), wherein said culturing produces neurospheres;
    (iii) obtaining cells from said neurospheres; and
    (iv) culturing said cells obtained from said neuro spheres in the presence of a G9a histone methyltransferase inhibitor (G9a HMTase) and a DNA methyltransferase (DMNT) inhibitor in an embryonic stem cell medium for a time sufficient to produce pluripotent cells from said cells obtained from said neurospheres, thereby reprogramming a somatic cell to produce induced pluripotent cells.

5. The method of claim 4, wherein the G9a HMTase inhibitor is BIX01294 and the DMNT inhibitor is RG108.

6. A method for reprogramming a somatic cell to produce pluripotent cells comprising:
    (i) transducing a somatic cell with a nucleic acid comprising the coding sequence for B cell-specific Moloney murine leukemia virus integration site 1 (Bmi-1) operably linked to a promoter, wherein said transducing results in overexpression of Bmi-1 protein in said somatic cell and produces a transduced somatic cell;
    (ii) culturing said transduced somatic cell in a medium comprising basic Fibroblast Growth Factor (bFGF) and is free of Epidermal Growth Factor (EGF), wherein said culturing produces neurospheres;
    (iii) obtaining cells from said neurospheres; and
    (iv) culturing said cells obtained from said neurospheres in the presence of a histone deacetylase (HDAC) inhibitor in an embryonic stem cell medium for a time sufficient to produce pluripotent cells from said cells obtained from said neurospheres, thereby reprogramming a somatic cell to produce induced pluripotent cells.

7. The method of claim 6, wherein the HDAC inhibitor is valproic acid (VPA).

* * * * *